United States Patent
Tsai et al.

(10) Patent No.: US 10,473,607 B2
(45) Date of Patent: Nov. 12, 2019

(54) GAS SENSOR

(71) Applicant: Winbond Electronics Corp., Taichung (TW)

(72) Inventors: Ming-Chih Tsai, Taichung (TW); Yu-Hsuan Ho, Taichung (TW)

(73) Assignee: Winbond Electronics Corp., Taichung (TW)

( * ) Notice: Subject to any disclaimer, the term of this patent is extended or adjusted under 35 U.S.C. 154(b) by 237 days.

(21) Appl. No.: 15/668,709

(22) Filed: Aug. 4, 2017

(65) Prior Publication Data

US 2018/0231481 A1   Aug. 16, 2018

(30) Foreign Application Priority Data

Feb. 13, 2017  (CN) .......................... 2017 1 0075991

(51) Int. Cl.
*G01N 27/12* (2006.01)
*G01N 27/04* (2006.01)
*G01N 33/00* (2006.01)

(52) U.S. Cl.
CPC ............. *G01N 27/12* (2013.01); *G01N 27/04* (2013.01); *G01N 27/125* (2013.01); *G01N 33/0036* (2013.01)

(58) Field of Classification Search
CPC ...... G01N 27/04; G01N 27/12; G01N 27/129; G01N 33/0009; G01N 33/0027; G01N 33/0036
USPC .............................................. 73/31.05, 31.06
See application file for complete search history.

(56) References Cited

U.S. PATENT DOCUMENTS

| | | | |
|---|---|---|---|
| 5,618,496 A * | 4/1997 | Hasumi | G01N 27/12 340/634 |
| 5,969,231 A * | 10/1999 | Qu | G01N 27/4075 338/34 |
| 8,835,180 B2 | 9/2014 | Gryska et al. | |
| 2008/0137063 A1* | 6/2008 | Naya | G01N 21/6428 356/36 |
| 2011/0031983 A1* | 2/2011 | David | G01N 27/125 324/663 |

FOREIGN PATENT DOCUMENTS

| | | |
|---|---|---|
| CN | 104730116 | 6/2015 |
| TW | 201616127 | 5/2016 |

\* cited by examiner

*Primary Examiner* — Benjamin R Schmitt
(74) *Attorney, Agent, or Firm* — JCIPRNET

(57) ABSTRACT

A gas sensor includes a first substrate, at least one first electrode, a sensing structure, at least one second electrode, and a second substrate. The at least one first electrode is located on the first substrate. The sensing structure is located on the at least one first electrode and the first substrate, and the sensing structure includes a first semiconductor layer and a second semiconductor layer. The first semiconductor layer having a first conductive type covers the first substrate and the at least one first electrode; the second semiconductor layer having a second conductive type is located on the first semiconductor layer. The at least one second electrode covers the sensing structure. The second substrate covers the at least one second electrode and the sensing structure.

11 Claims, 5 Drawing Sheets

GAS SENSOR

CROSS-REFERENCE TO RELATED APPLICATION

This application claims the priority benefit of China application serial no. 201710075991.3, filed on Feb. 13, 2017. The entirety of the above-mentioned patent application is hereby incorporated by reference herein and made a part of this specification.

BACKGROUND OF THE INVENTION

Field of the Invention

The invention relates to a gas sensor, particularly a gas sensor capable of measuring a variety of interfaces/junctions.

Description of Related Art

Conventional semiconductor gas sensors are capable of detecting different types of gases according to different sensing materials used by the gas sensors.

It is difficult, however, to form various types of sensors on a single substrate through performing the conventional semiconductor manufacturing process due to the high manufacturing costs resulting from the requirement for multiple photomasks in the semiconductor manufacturing process for. Moreover, the conventional semiconductor manufacturing process requires several chambers for performing manufacturing processes on a variety of materials. By contrast, manufacturing a variety of materials in a single chamber easily results in problems of cross contamination.

SUMMARY OF THE INVENTION

The invention provides a gas sensor capable of manufacturing and preparing a variety of materials in a single chamber, making it easier to form various types of sensors on a single substrate.

The invention provides a gas sensor capable of measuring a variety of interfaces/junctions to increase the selectivity and the sensitivity of the gas sensor.

The invention provides a gas sensor including a first substrate, at least one first electrode, a sensing structure, at least one second electrode, and a second substrate. The at least one first electrode is located on the first substrate. The sensing structure is located on at least one first electrode and the first substrate. The sensing structure includes a first semiconductor layer and a second semiconductor layer, wherein the first semiconductor layer is located on the at least one first electrode and has a first conductive type. The second semiconductor layer is located on the first semiconductor layer and has a second conductive type. The at least one second electrode covers the sensing structure. The second substrate covers the at least one second electrode and the sensing structure.

In an embodiment of the invention, each of the first substrate and the second substrate includes a porous material.

In an embodiment of the invention, the at least one first electrode and the at least one second electrode respectively extend into holes of the first substrate and the second substrate.

In an embodiment of the invention, a material of either the first semiconductor layer or the second semiconductor layer includes an n-type semiconductor material, and a material of the other of the first semiconductor layer and the second semiconductor layer includes a p-type semiconductor material.

In an embodiment of the invention, the first semiconductor layer is in direct contact with the second semiconductor layer.

In an embodiment of the invention, the at least one first electrode includes a plurality of first electrodes, and the at least one second electrode includes a plurality of second electrodes.

In an embodiment of the invention, the plurality of first electrodes include a first interdigital electrode and a second interdigital electrode. The first interdigital electrode includes a first main body and a plurality of first extensions. The second interdigital electrode includes a second main body and a plurality of second extensions. The first main body is disposed opposite to the second main body, and the plurality of first extensions and the plurality of second extensions are alternately arranged.

In an embodiment of the invention, the plurality of second electrodes include a third interdigital electrode and a fourth interdigital electrode. The third interdigital electrode includes a third main body and a plurality of third extensions. The fourth interdigital electrode includes a fourth main body and a plurality of fourth extensions. The third main body is disposed opposite to the fourth main body, and the plurality of third extensions and the plurality of fourth extensions are alternately arranged.

In an embodiment of the invention, a method for forming the first substrate, the at least one first electrode, the sensing structure, the at least one second electrode, or the second substrate includes a three-dimensional printing method, an ink-jet printing method, or a combination thereof.

In an embodiment of the invention, the at least one first electrode or the at least one second electrode includes an end point connected to an external circuit.

In an embodiment of the invention, a method for forming the first substrate and the second substrate includes an imprinting method, a vacuum filtration method, or a combination thereof.

In an embodiment of the invention, a method for forming the at least one first electrode, the first semiconductor layer, the second semiconductor layer, and the at least one second electrode includes a three-dimensional printing method, an ink-jet printing method, or a combination thereof.

Based on the above, the gas sensor provided herein is capable of forming various types of gas sensors on a single substrate through performing the three-dimensional printing method. The three-dimensional printing method only requires the replacement of one ink with another according to the materials to be manufactured. Thereby, the problem of cross contamination is avoided when various materials are manufactured and prepared in a single chamber. That is to say, the gas sensor described in the invention does not require the manufacture of multiple photomasks which is required in the conventional semiconductor manufacturing process, so as to reduce the manufacturing costs and enhance stability. Moreover, the gas sensor provided in the invention includes semiconductor layers of different conductive types, leading to its capability of measuring a variety of interfaces. As a result, the selectivity and the sensitivity of the gas sensor are increased.

To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate exemplary embodiments of the invention and, together with the description, serve to explain the principles of the invention.

DESCRIPTION OF THE EMBODIMENTS

Figure 1:
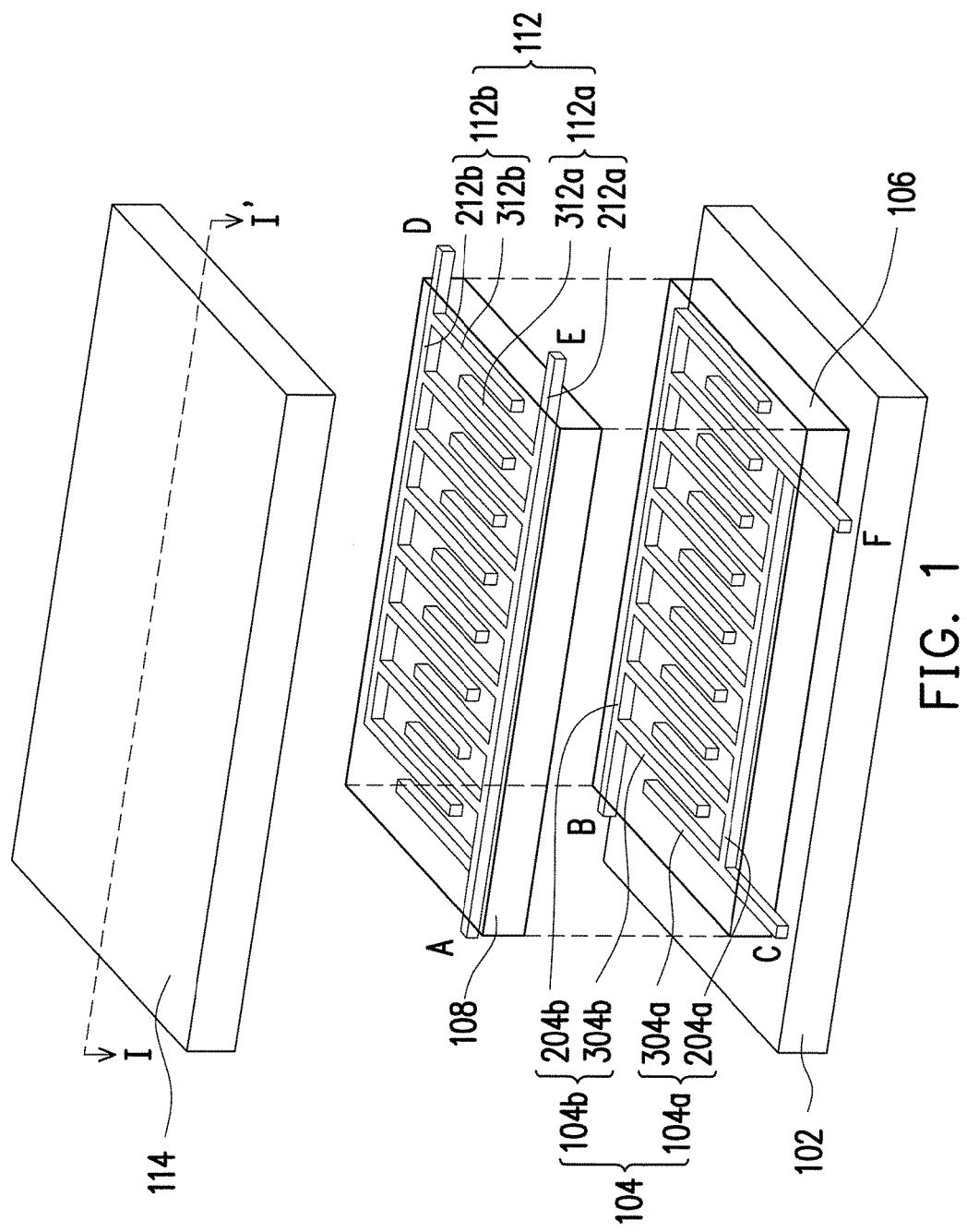
FIG. 1 is a schematic three-dimensional exploded view of a gas sensor in an embodiment of the invention.
Figure 2:
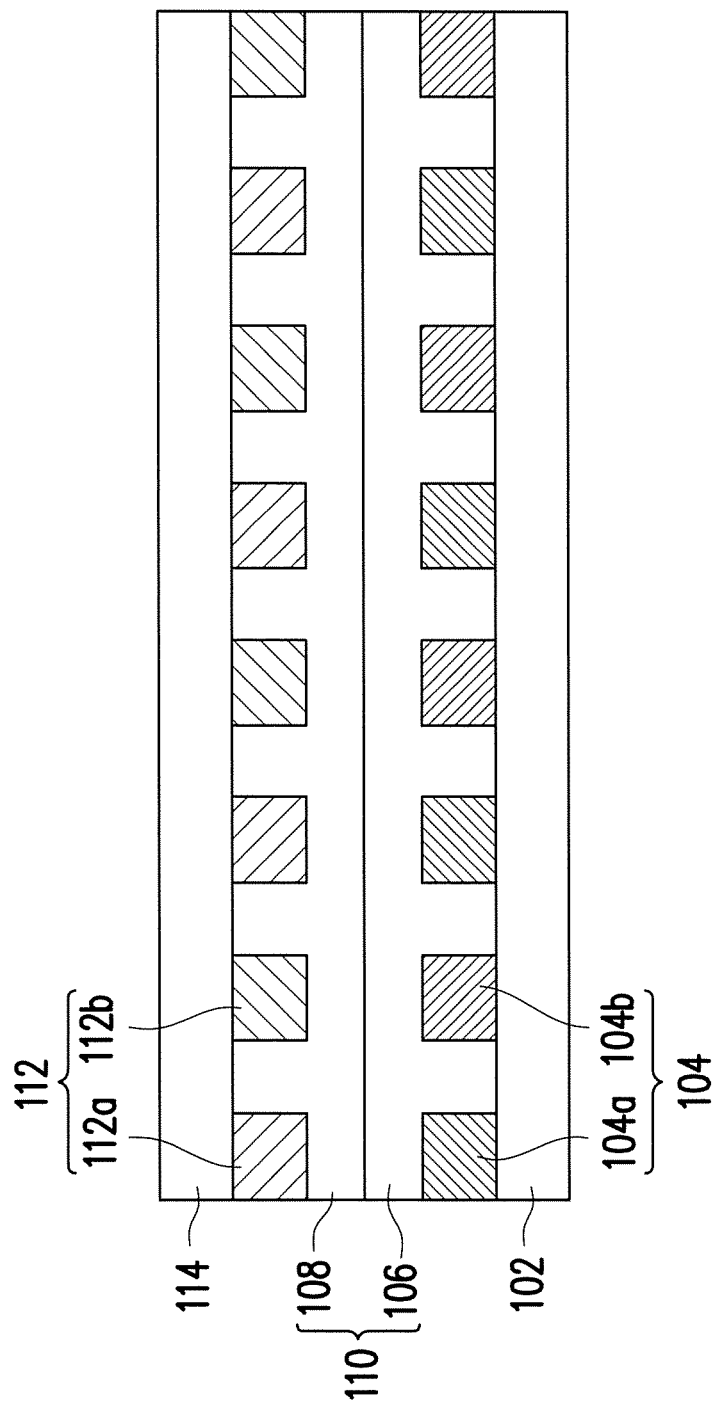
FIG. 2 is a schematic cross-sectional view taken along the section line I-I' in FIG. 1.

FIG. 1 is a schematic three-dimensional exploded view of a gas sensor in an embodiment of the invention. FIG. 2 is a schematic cross-sectional view taken along the section line I-I' in FIG. 1.

Please refer to FIG. 1 and FIG. 2. A gas sensor 100 in an embodiment of the invention includes a first substrate 102, at least one first electrode 104, a sensing structure 110, at least one second electrode 112, and a second substrate 114. The first substrate 102 may be, for instance, a flexible substrate or a rigid substrate. For example, a material of the first substrate 102 may be glass, polyethylene terephthalate (PET), polyethylene naphthalate (PEN), polyimide (PI), polyvinyl chloride (PVC), polypropylene (PP), cyclo olefin polymer (COP), polyethylene (PE), or a combination thereof. Furthermore, the material of the first substrate 102 may also be a commercially available filtration membrane as a porous substrate, for instance, paper, glass fiber, aluminum oxide, polypropylene (PP), perfluoro sulfonic acid polymer, nanocellulose, cellulose acetate, polysulfone, polyvinylamine, polyamide, polyfuran, etc. In some embodiments of the invention, a surface of the first substrate 102 is a planar surface. In other embodiments of the invention, however, a surface of the first substrate 102 is a non-planar surface, e.g., a curved surface, a concave surface, an inclined surface, or a combination thereof. A method for forming the first substrate 102 includes purchasing a commercially available membrane which contain a filtration layer or contain a filtration layer and a supporting layer, extrusion molding, injection molding, blow molding, electrospinning, desiccation, coating, anode oxidation, phase inversion, imprint, vacuum filtration, three-dimensional printing, ink-jet printing, or a combination thereof.

The first electrode 104 is located on the first substrate 102. In the embodiment of the invention, the number of the first electrodes 104 is plural, and the first electrodes 104 are disposed separately on the first substrate 102. Nevertheless, the invention is not limited to the above. The first electrode 104 may be, for example, an interdigital electrode. To be more specific, the first electrode 104 includes a first electrode 104a and a first electrode 104b. The first electrode 104a and the first electrode 104b are both interdigital electrodes. In an embodiment of the invention, the interdigital electrode may have main bodies 204a and 204b extending towards one direction and a plurality of extensions 304a and 304b extending towards another direction. In the embodiment of the invention, the main body 204a of the first electrode 104a is disposed opposite to the main body 204b of the first electrode 104b, and the extension 304a of the first electrode 104a and the extension 304b of the first electrode 104b are alternately arranged. Nevertheless, the invention is not limited to the above.

A material of the first electrode 104 includes a conductive material. The conductive material may be a metal or an alloy, such as silver (Ag), gold (Au), copper (Cu), platinum (Pt), aluminum (Al), or a combination thereof. A method for forming the first electrode 104 may be, for example, a three-dimensional printing method, an ink jet printing method, or a combination thereof.

The sensing structure 110 is formed on the first substrate 102 and the first electrode 104. The sensing structure 110 includes a first semiconductor layer 106 and a second semiconductor layer 108. The first semiconductor layer 106 has a first conductive type and is located on the first substrate 102 and the first electrode 104. The second semiconductor layer 108 has a second conductive type and is located on the first semiconductor layer 106. In an embodiment of the invention, the first conductive type is different from the second conductive type, and the first semiconductor layer 106 is in direct contact with the second semiconductor layer 108, so that the sensing structure 110 is capable of measuring a variety of interfaces/junctions. For instance, the first semiconductor layer 106 may be a p-type semiconductor layer, and the second semiconductor layer 108 may be an n-type semiconductor layer. The first semiconductor layer 106 is in direct contact with the second semiconductor layer 108. Thereby, the sensing structure 110 is capable of measuring the p-type interface, the n-type interface, and a p-n junction.

Furthermore, in an embodiment of the invention, the first semiconductor layer 106 is not only formed on the first electrode 104 but in a gap between the two adjacent first electrodes 104a and 104b, so as to expand the contact area between the first electrode 104 and the first semiconductor layer 106.

A material of the first semiconductor layer 106 and the second semiconductor layer 108 may be, for example, an n-type semiconductor material or a p-type semiconductor material. To be more specific, in some embodiments of the invention, the material of the first semiconductor layer 106 is an n-type material, and the material of the second semiconductor layer 108 is a p-type material. In other embodiments of the invention, however, the first semiconductor layer 106 is a p-type semiconductor material, and the second semiconductor layer 108 is an n-type semiconductor material. The n-type semiconductor material may be, for example, zinc oxide (ZnO), titanium dioxide ($TiO_2$), zirconium dioxide ($ZrO_2$), hafnium oxide ($HfO_2$), tin dioxide ($SnO_2$), iron oxide ($Fe_2O_3$), tungsten trioxide ($WO_3$), molybdenum trioxide ($MoO_3$), vanadium pentoxide ($V_2O_5$), or a combination thereof. The p-type semiconductor material may be, for example, nickel oxide (NiO), copper oxide (CuO), cobalt oxide (CoO), or a combination thereof.

The sensing structure 110 is capable of detecting gas, such as nitric oxide (NO), nitric dioxide ($NO_2$), ammonia ($NH_3$), hydrogen ($H_2$), water ($H_2O$), sulfur dioxide ($SO_2$), hydrogen sulfide ($H_2S$), oxygen ($O_2$), ozone ($O_3$), carbon monoxide (CO), methane ($CH_4$), ethylene ($C_2H_4$), acetylene ($C_2H_2$), chlorine ($Cl_2$), and volatile organic compounds (VOC). Common VOC include, for example, methanol ($CH_3OH$) and ethanol ($C_2H_5OH$) of alcohols, acetone ($C_3H_6O$) of ketones, formaldehyde of aldehydes, benzene, toluene, xylene, ethylbenzene, and styrene of the benzene group, or a combination thereof.

A method for forming the first semiconductor layer 106 and the second semiconductor layer 108 may be, for example, a three-dimensional printing method, an ink-jet printing method, or a combination thereof. Both the three-dimensional printing and the ink-jet printing methods simply require the replacement of one ink with another according to different materials to be manufactured. Thereby, forming the first semiconductor layer 106 and the second semiconductor layer 108 on the first substrate 102 and the first electrode 104 in a single chamber does not lead to the problem of cross contamination. As a result, the issue of the difficulty in forming various types of sensors on a single substrate in the conventional semiconductor manufacturing process is solved.

The second electrode 112 covers the sensing structure 110. In the embodiment of the invention, the number of the second electrodes 112 is plural, and the second electrodes 112 are disposed separately on the sensing structure 110. Nevertheless, the invention is not limited to the above. The second electrode 112 may be, for example, an interdigital electrode. To be more specific, the second electrode 112 includes a second electrode 112a and a second electrode 112b. In some embodiments of the invention, the second electrode 112a and the second electrode 112b are both interdigital electrodes. The interdigital electrode may have main bodies 212a and 212b and a plurality of extensions 312a and 312b. The main bodies 212a and 212b extend towards a first direction while the extensions 312a and 312b extend towards a second direction. The first direction is different from the second direction. In some embodiments of the invention, the first direction and the second direction are perpendicular to each other. In the embodiment of the invention, the main body 212a of the second electrode 122a is disposed opposite to the main body 212b of the second electrode 112b, and the extension 312a of the second electrode 112a and the extension 312b of the second electrode 112b are alternately arranged. Nevertheless, the invention is not limited to the above.

A material of the second electrode 112 includes a conductive material. The conductive material may be a metal or an alloy, such as Ag, Au, Cu, Pt, Al, or a combination thereof. A method for forming the second electrode 112 may be, for example, a three-dimensional printing method, an ink-jet printing method, or a combination thereof.

Furthermore, the second semiconductor layer 112 is also located in a gap between the two adjacent second electrodes 112a and 112b, so as to expand a contact area between the second electrode 112 and the second semiconductor layer 108.

The second substrate 114 covers the second electrode 112 and the sensing structure 110. The second substrate 114 may be, for instance, a flexible substrate or a rigid substrate. For example, a material of the second substrate 114 may be glass, PET, PEN, PI, PVC, PP, COP, PE, or a combination thereof. Furthermore, the material of the second substrate 114 may also be a commercially available filtration membrane as a porous substrate, for instance, paper, glass fiber, aluminum oxide, polypropylene, perfluoro sulfonic acid polymer, nanocellulose, cellulose acetate, polysulfone, polyvinylamine, polyamide, polyfuran, etc. A method for forming the second substrate 114 includes an imprint method, a vacuum filtration method, a three-dimensional printing method, an ink-jet printing method, or a combination thereof.

To more specifically describe the capability of measuring a variety of interfaces/junctions of the gas sensor 100, the gas sensor in FIG. 1 is exemplified hereinafter.

Please refer to FIG. 1. The first electrodes 104a and 104b are separated from each other and disposed on the first substrate 102. The first semiconductor layer 106 is located on and between the first electrode 104a and the first electrode 104b. The first electrodes 104a and 104b respectively include a single end point or a plurality of end points connected to an external circuit. In an embodiment of the invention, the first electrode 104 has end points C and F that are connected to an external circuit. The first electrode 104b has an end point B connected to an external circuit. In the embodiment disclosing that the first semiconductor layer 106 is a p-type semiconductor material, the first semiconductor layer 106 and the first electrodes 104a and 104b construct a p-type sensor. Thereby, in case that the distance between the first electrodes 104a and 104b is known, the types of gas, the concentration of gas, or a combination of the types and the concentration of gas may be detected through measuring changes between the end points B and C, e.g., the changes of electric resistance, voltage, current, and so on.

To be more specific, the gas that can be detected by the p-type sensor includes NO, $NO_2$, $NH_3$, $H_2$, $H_2O$, $SO_2$, $H_2S$, $O_2$, $O_3$, CO, $CH_4$, $C_2H_4$, $C_2H_2$, $Cl_2$, and VOC. Common VOCs are, for example, $CH_3OH$ and $C_2H_5OH$ of alcohols, $C_3H_6O$ of ketones, formaldehyde of aldehydes, benzene, toluene, xylene, ethylbenzene, and styrene from the benzene group, or a combination thereof. Moreover, a range of gas concentration which can be detected by the p-type sensor is, for example, between 10 ppb to 100000 ppm.

The second electrodes 112a and 112b are separated from each other and disposed on the second semiconductor layer 108, and the second semiconductor layer 108 is located between the second electrode 112a and the second electrode 112b. The second electrodes 112a and 112b respectively include a single end point or a plurality of end points connected to an external circuit. In an embodiment of the invention, the second electrode 112 has end points A and E that are connected to an external circuit. The second electrode 112b has an end point D connected to an external circuit. In the embodiment disclosing that the second semiconductor layer 108 is an n-type semiconductor material, the second semiconductor layer 108 and the second electrodes 112a and 112b construct an n-type sensor. Thereby, in case that the distance between the second electrodes 112a and 112b is known, the types of gas, the concentration of gas, and a combination of the types and the concentration of gas may be detected through measuring changes between the end points D and E, such as the changes of electric resistance, voltage, current, and so on.

To be more specific, the n-type sensor is capable of detecting gas, such as NO, $NO_2$, $NH_3$, $H_2$, $H_2O$, $SO_2$, $H_2S$, $O_2$, $O_3$, CO, $CH_4$, $C_2H_4$, $C_2H_2$, $Cl_2$, and VOC. Common VOCs are, for example, $CH_3OH$ and $C_2H_5OH$ of alcohols, $C_3H_6O$ of ketones, formaldehyde of aldehydes, benzene, toluene, xylene, ethylbenzene, and styrene from the benzene group, or a combination thereof. Moreover, a range of gas concentration that may be detected by the n-type sensor is, for example, between 10 ppb to 100000 ppm.

In an embodiment of the invention, the first semiconductor layer 106 including a p-type semiconductor material is in direct contact with the second semiconductor layer 108 including an n-type semiconductor material. The first electrode 104 and the second electrode 112 thus construct a p-n junction sensor. Thereby, in case that the distance between the first electrode 104 and the second electrode 112 is known, the types of gas, the concentration of gas, and a combination of the types and the concentration of gas may be detected through measuring changes between the end points A and F, such as the changes of electric resistance, voltage, current, and so on.

To be more specific, the gas that can be detected by the p-n junction sensor includes NO, $NO_2$, $NH_3$, $H_2$, $H_2O$, $SO_2$, $H_2S$, $O_2$, $O_3$, CO, $CH_4$, $C_2H_4$, $C_2H_2$, $Cl_2$, and VOC. Common VOCs are, for example, $CH_3OH$ and $C_2H_5OH$ of alcohols, $C_3H_6O$ of ketones, formaldehyde of aldehydes, benzene, toluene, xylene, ethylbenzene, and styrene from the benzene group, or a combination thereof. Moreover, a range of gas concentration which can be detected by the p-n junction sensor is, for example, between 10 ppb to 100000 ppm.

Based on the above, the gas sensor 100 in an embodiment of the invention is capable of measuring n-type, p-type, and p-n junctions. In other words, the gas sensor 100 is capable of increasing its selectivity and sensitivity by forming various types of sensors on a single substrate.

Please refer to FIG. 2. A method for manufacturing a gas sensor 100 in an embodiment of the invention includes following steps. At least one first electrode 104 is formed on a first substrate 102. A sensing structure 110 is formed on the first substrate 102 and the at least one first electrode 104. Steps of forming the sensing structure 110 include forming a first semiconductor layer 106 of a first conductive type on the first substrate 102 and the first electrode 104 and forming a second semiconductor layer 108 of a second conductive type on the first semiconductor layer 106. At least one second electrode 112 is formed on the sensing structure 110. The second substrate 114 covers the second electrode 112 and the sensing structure 110.

In an embodiment of the invention, a method for forming the first substrate 102 and the second substrate 114 includes, for example, purchasing the commercially available membrane which contains a filtration membrane or a filtration membrane and a supporting membrane, extrusion molding, injection molding, blow molding, electrospinning, desiccation, coating, anode oxidation, phase inversion, imprint, vacuum filtration, three-dimensional printing, ink-jet printing, or a combination thereof.

In an embodiment of the invention, the step of forming the first electrode 104, the first semiconductor layer 106, the second semiconductor layer 108, and the second electrode 112 is, for example, three-dimensional printing, ink jet printing, or a combination thereof. The three-dimensional printing method and the ink-jet printing method only require the replacement of one ink with another according to different materials to be manufactured. Thereby, the problem of cross contamination is avoided when the first semiconductor layer 106 and the second semiconductor layer 108 made of different materials are formed on the first substrate 102 and the first electrode 104 in a single chamber. As a result, the issue of the difficulty in forming various types of sensors on a single substrate in the conventional semiconductor manufacturing process may be solved.

Furthermore, in some embodiments of the invention, the first electrode 104, the first semiconductor layer 106, the second semiconductor layer 108, and the second electrode 112 are formed by applying the same step. In other embodiments of the invention, the first electrode 104, the first semiconductor layer 106, the second semiconductor layer 108, and the second electrode 112 are formed by different methods.

It should be noted that the three-dimensional printing method and the ink-jet printing method may be applied to form the first electrode 104, the first semiconductor layer 106, the second semiconductor layer 108, and the second electrode 112 on a curved surface, a concave surface, an inclined surface, a combination of said surfaces, or a surface similar to the above, which can hardly be achieved by applying the conventional manufacturing process.

Figure 3A:
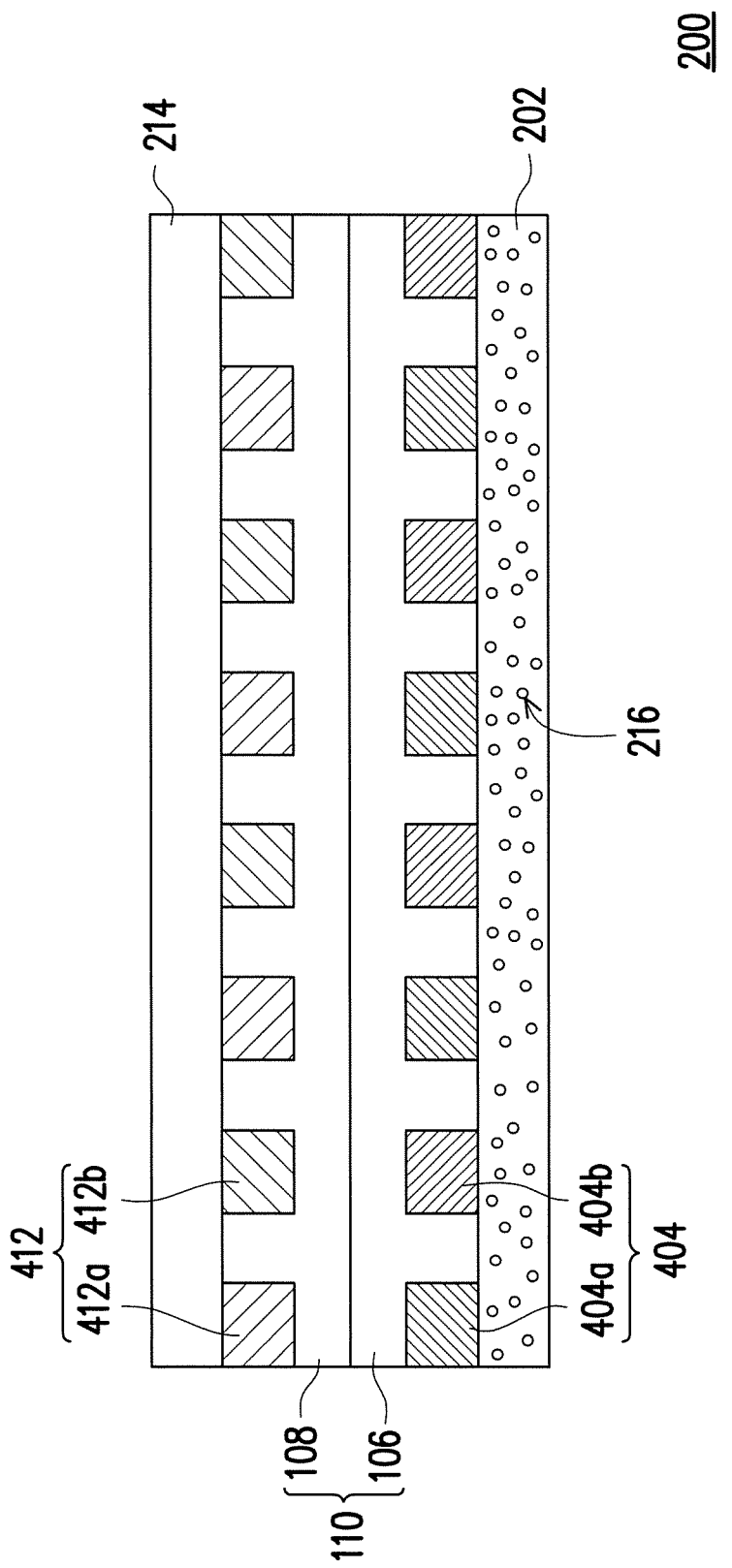
FIGS. 3A to 3C are schematic cross-sectional views of gas sensors in different embodiments of the invention.
Figure 3B:
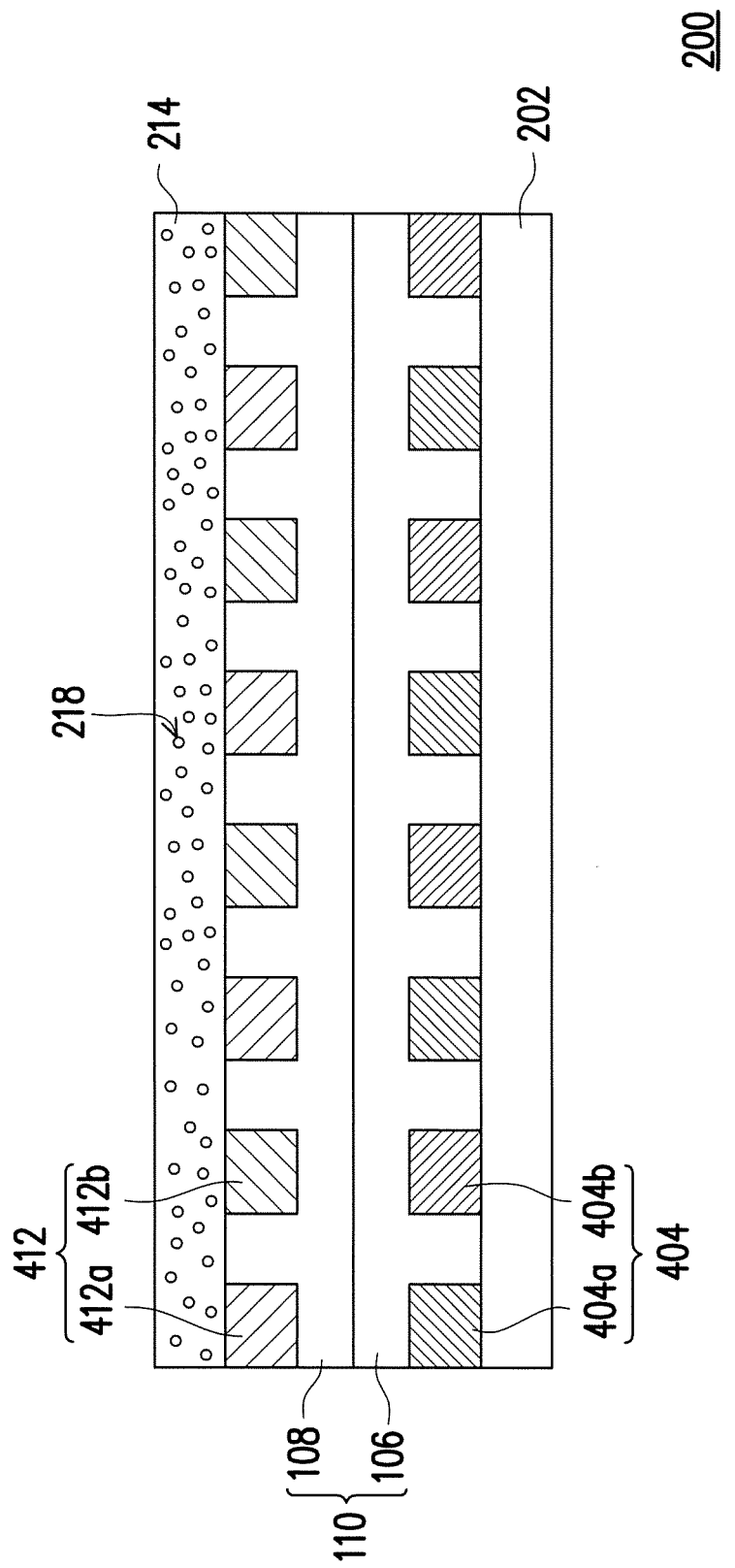
Figure 3C:
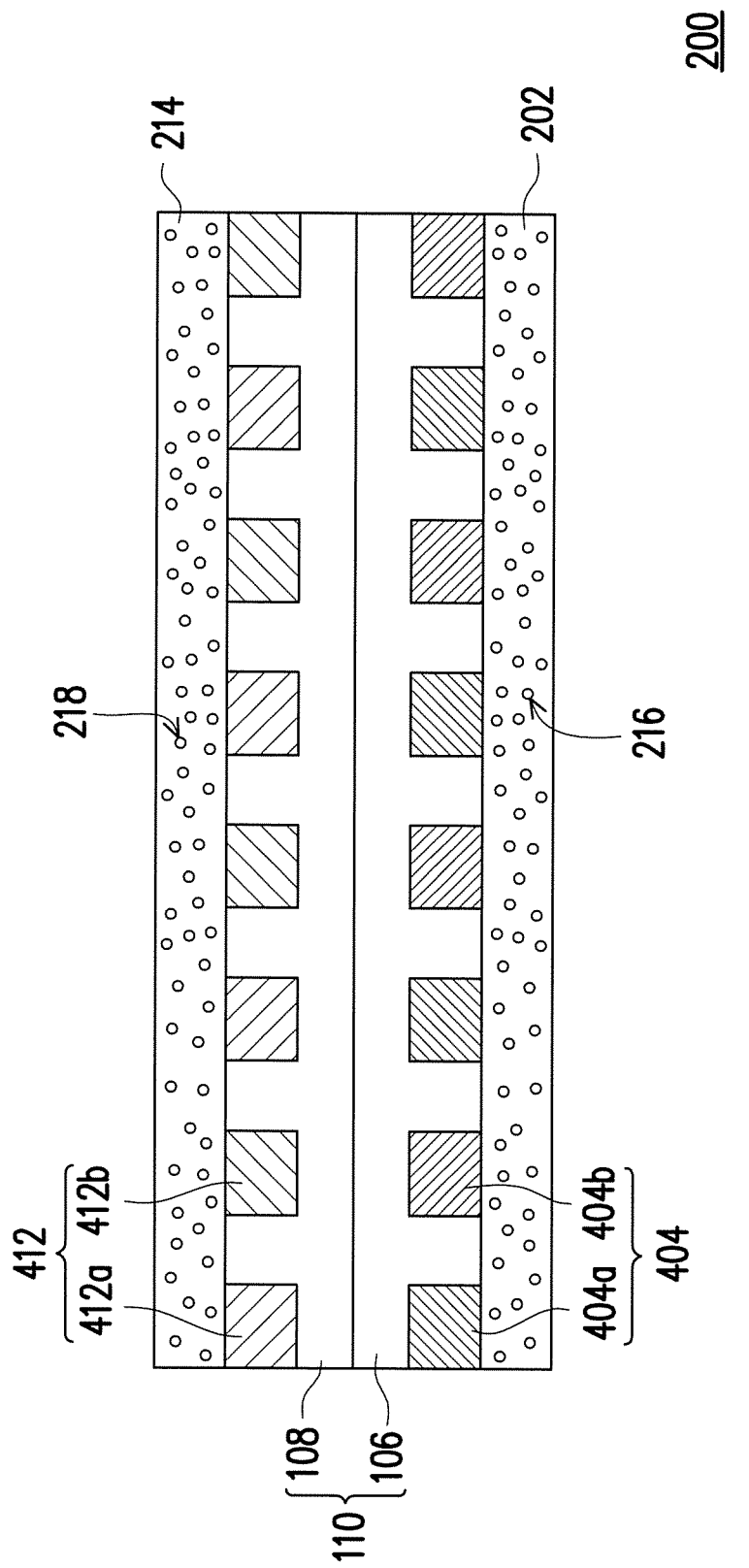

FIGS. 3A to 3C are schematic cross-sectional views of a gas sensor 200 in different embodiments of the invention. The gas sensor 200 overall resembles the gas sensor 100, while the difference therebetween lies in that a first substrate 202 or a second substrate 214 of the gas sensor 200 include a hole. Identical or similar elements of the gas sensors 100 and 200 are marked with the identical or similar reference numbers. The connection relations, the materials, and the manufacturing processes of the other components are specifically described above and thus are no longer explained in the following paragraphs.

Please refer to FIGS. 3A to 3C. A gas sensor 200 in different embodiments of the invention includes a first substrate 202, at least one first electrode 404, a sensing structure 110, at least one second electrode 412, and a second substrate 214. Both or either of the first substrate 202 and the second substrate 214 may include a hole.

As shown in FIGS. 3A and 3B, either of the first substrate 202 and the second substrate 214 includes a hole in some embodiments of the invention. For instance, the first substrate 202 includes a hole 216 as shown in FIG. 3A. The first electrode 404 may thus extend into the hole 216 of the first substrate 202 to increase an adhesive force between the first electrode 404 and the first substrate 202. Stability of the gas sensor 200 is thereby increased. Furthermore, the second substrate 214 may also include a hole 208 as shown in FIG. 3B. The second electrode 412 may thus extend into the hole 218 of the second substrate 214 to increase an adhesive force between the second electrode 412 and the second substrate 214. Stability of the gas sensor 200 is thereby increased.

As shown in FIG. 3C, the first substrate 202 and the second substrate 214 may include holes 216 and 218 respectively in some embodiments of the invention. As a result, the first electrode 404 and the second electrode 412 may extend into the holes 216 and 218 on the first substrate 202 and the second substrate 214 respectively to increase the adhesive forces both between the first electrode 404 and the first substrate 202 and between the second electrode 412 and the second substrate 214. Stability of the gas sensor 200 is thereby further increased.

A material of the first substrate 202 and the second substrate 214 may be, for instance, paper, glass fiber, aluminum oxide, polypropylene, perfluoro sulfonic acid polymer, nanocellulose, cellulose acetate, polysulfone, polyvinylamine, polyamide, polyfuran, etc. A method for forming the first substrate 202 and the second substrate 214 includes purchasing the commercially available membrane which contains a filtration membrane or a filtration membrane and a supporting membrane, spray printing through conducting a three-dimensional printing method, extrusion molding, injection molding, blow molding, electrospinning, desiccation, coating, anode oxidation, phase inversion, imprint, vacuum filtration, or a combination thereof.

To sum up, in the gas sensor described in the invention, various types of sensors are formed on a single substrate through three-dimensional printing that only requires the replacement of one ink with another according to different materials to be manufactured. Thereby, the problem of cross contamination is avoided when various materials are manufactured and prepared in a single chamber. That is to say, the gas sensor described in the invention does not require the manufacture of multiple photomasks in the conventional semiconductor manufacturing process, so as to reduce the manufacturing costs and increase stability. Moreover, the gas sensor provided herein includes the semiconductor layers of different conductive types, leading to its capability of measuring a variety of interfaces. The selectivity and the sensitivity of the gas sensor are thus increased. Furthermore, the first substrate and the second substrate of the gas sensor are made of porous materials, enabling the first electrode and the second electrode to extend into the holes of the first substrate and the second substrate. The adhesive forces between the electrodes and the substrates are thereby increased.

It will be apparent to those skilled in the art that various modifications and variations can be made to the disclosed embodiments without departing from the scope or spirit of this invention. In view of the foregoing, it is intended that the invention covers modifications and variations provided that they fall within the scope of the following claims and their equivalents.

What is claimed is:

1. A gas sensor comprising:
   at least one first electrode located on a first substrate, wherein the at least one first electrode comprises a plurality of first electrodes spaced apart from each other;
   a sensing structure located on the at least one first electrode and on the first substrate, the sensing structure comprising:
      a first semiconductor layer, having a first conductive type and covering the first substrate and the at least one first electrode, wherein the first semiconductor layer is located between two adjacent first electrodes to form a first interface of the first conductive type; and
      a second semiconductor layer, having a second conductive type and located on the first semiconductor layer, wherein a junction of the first conductive type and the second conductive type is formed between the first semiconductor layer and the second semiconductor layer;
   at least one second electrode, covering the sensing structure, wherein the at least one second electrode comprises a plurality of second electrodes spaced apart from each other, and the second semiconductor layer is located between two adjacent second electrodes to form a second interface of the second conductive type; and
   a second substrate, covering the at least one second electrode and the sensing structure
   wherein the two adjacent first electrodes and the first semiconductor layer therebetween construct a first sensor having the first interface of the first conductive type,
   the two adjacent second electrodes and the second semiconductor layer therebetween construct a second sensor having the second interface of the second conductive type, and
   the at least one first electrode, the at least one second electrode, the first semiconductor layer and the second semiconductor layer construct a third sensor having the junction of the first conductive type and the second conductive type.

2. The gas sensor according to claim 1, the first substrate and the second substrate both comprise a porous material.

3. The gas sensor according to claim 2, wherein the at least one first electrode and the at least one second electrode respectively extend into holes of the first substrate and the second substrate.

4. The gas sensor according to claim 1, wherein a material of either the first semiconductor layer or the second semiconductor layer comprises an n-type semiconductor material, and a material of the other of the first semiconductor layer and the second semiconductor layer comprises a p-type semiconductor material.

5. The gas sensor according to claim 4, wherein the first semiconductor layer is in direct contact with the second semiconductor layer.

6. The gas sensor according to claim 1, wherein the plurality of first electrodes comprise a first interdigital electrode and a second interdigital electrode, the first interdigital electrode comprises a first main body and a plurality of first extensions, and the second interdigital electrode comprises a second main body and a plurality of second extensions,
   wherein the first main body is disposed opposite to the second main body, and the plurality of first extensions and the plurality of second extensions are alternately arranged.

7. The gas sensor according to claim 6, wherein the plurality of the second electrodes comprise a third interdigital electrode and a fourth interdigital electrode, the third interdigital electrode comprises a third main body and a plurality of third extensions, and the fourth interdigital electrode comprises a fourth main body and a plurality of fourth extensions,
   wherein the third main body is disposed opposite to the fourth main body, and the plurality of third extensions and the plurality of fourth extensions are alternately arranged.

8. The gas sensor according to claim 1, wherein the at least one first electrode or the at least one second electrode comprises an end point connected to an external circuit.

9. The gas sensor according to claim 1, wherein each of the first electrodes has a first endpoint connected to an external circuit.

10. The gas sensor according to claim 9, wherein each of the second electrodes has a second endpoint connected to the external circuit.

11. The gas sensor according to claim 1, wherein the first semiconductor layer and the second semiconductor layer are formed on the first substrate and the at least one first electrode in a single chamber.

* * * * *